United States Patent [19]

Hirsch et al.

[11] Patent Number: 4,560,695
[45] Date of Patent: Dec. 24, 1985

[54] ISOXAZOLYL AND ISOTHIAZOLYL AROMATASE INHIBITORS

[75] Inventors: Kenneth S. Hirsch, New Palestine; Charles D. Jones; Harold M. Taylor, both of Indianapolis; Mark A. Winter, Indianapolis, all of Ind.

[73] Assignee: Eli Lilly and Company, Indianapolis, Ind.

[21] Appl. No.: 621,596

[22] Filed: Jun. 18, 1984

[51] Int. Cl.[4] .................. A61K 31/42; A61K 31/425; C07D 261/08; C07D 275/02
[52] U.S. Cl. .................................... 514/372; 514/378; 546/275; 546/280; 548/206; 548/214; 548/247
[58] Field of Search .................. 548/206, 214, 247; 514/372, 378; 424/272; 546/275, 280

[56] References Cited

U.S. PATENT DOCUMENTS

| | | | |
|---|---|---|---|
| 3,709,901 | 1/1973 | Draber et al. | 260/310 R |
| 3,764,690 | 10/1973 | Draber et al. | 424/273 |
| 3,794,653 | 2/1974 | Draber et al. | 260/296 R |
| 3,852,056 | 12/1974 | Draber et al. | 71/76 |
| 3,897,438 | 7/1975 | Draber et al. | 260/296 R |

OTHER PUBLICATIONS

Ashton, et al., "Heterocyclic Analogs of Chlorcyclazme", Chem. Abst. 101:130647(f) (1984).
Vita-Finzi, et al., "Reaction of Benzonitrile Oxides . . . ", Chem. Abst. 62:14646(d) (1965).

*Primary Examiner*—Donald G. Daus
*Assistant Examiner*—G. Hendricks
*Attorney, Agent, or Firm*—Charles W. Ashbrook; Arthur R. Whale

[57] ABSTRACT

This invention provides certain isoxazole and isothiazole derivatives, their pharmaceutical formulations, and their use in inhibiting aromatase and treating or preventing estrogen-dependent diseases in mammals.

12 Claims, No Drawings

4,560,695

ISOXAZOLYL AND ISOTHIAZOLYL AROMATASE INHIBITORS

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide certain azole derivatives, their pharmaceutical formulations, and their use in a method for inhibiting the enzyme aromatase in mammals. The invention thus provides for the treatment or prevention of breast cancer and other estrogen-dependent diseases.

SUMMARY OF THE INVENTION

This invention provides compounds of the formula

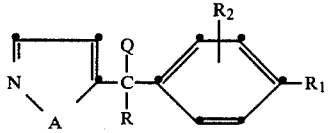

I wherein:
A is S or O;
R is pyridyl or

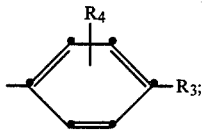

Q is hydrogen, hydroxy, halo, or methyl; and
$R_1$, $R_2$, $R_3$, and $R_4$ are independently hydrogen, halo, $C_1$-$C_3$ alkyl, $C_1$-$C_3$ alkoxy, nitro, or trifluoromethyl, and pharmaceutically acceptable salts thereof.

In addition, this invention provides a method of inhibiting aromatase in mammals which comprises administering to said mammal an aromatase inhibiting amount of a compound of the above formula. By virtue of their ability to inhibit the enzyme aromatase, the compounds of the above formula are useful in the treatment and prevention of estrogen-dependent diseases, especially breast cancer, in mammals.

Further provided by this invention are pharmaceutical formulations comprising one or more of the compounds of the above formula in combination with a suitable pharmaceutical carrier, diluent, or recipient therefor. The formulations provided by this invention are particularly useful in treating mammals suffering from estrogen-dependent diseases such as breast cancer.

DETAILED DESCRIPTION AND PREFERRED EMBODIMENT

The term "$C_1$-$C_3$ alkyl" refers to methyl, ethyl, propyl, and isopropyl. The term "$C_1$-$C_3$ alkoxy" refers to methoxy, ethoxy, propoxy, or isopropoxy. The term "halo" refers to fluoro, chloro, bromo, and iodo. "Pyridyl" refers to 2-, 4-, or especially 3-pyridyl.

A preferred group of compounds useful in the method of this invention are those wherein:
(a) A is S,
(b) Q is hydrogen or hydroxy,
(c) R is substituted phenyl, and
(d) $R_1$ and $R_3$ are independently halo, especially fluoro or chloro, or trifluoromethyl.

As will be recognized by those skilled in the art, many of the compounds of this invention contain an asymmetric carbon atom. This invention is not limited to any particular isomer but includes the individual enantiomers as well as the racemates of the compounds of Formula I.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The compounds of Formula I may be prepared by any of several methods known in the art. One general method of preparing the carbinol compounds of Formula I is as follows:

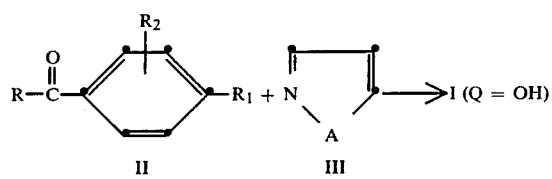

According to the above scheme, isoxazole or isothiazole (III) is treated with a strong base, such as an alkyl alkali metal, for example, n-butyl lithium, in a non-reactant solvent, such as an ether, for example tetrahydrofuran, to prepare the alkali metal derivative of the azole III. Once formed, the alkali metal derivative of III is treated with ketone II to provide the corresponding compound of Formula I wherein Q is hydroxy. Approximately equimolar amounts of II and azole III are employed, although other ratios are operative. The alkali metal derivative of III is generally prepared at temperatures from about −80° to 0° C. and the subsequent reaction with II is generally carried out at temperatures from about 0°–60° C. Under these conditions, the reaction is generally complete within about 4–8 hours.

A general method for preparing the halo compounds of Formula I (Q=halo) is summarized by the following scheme:

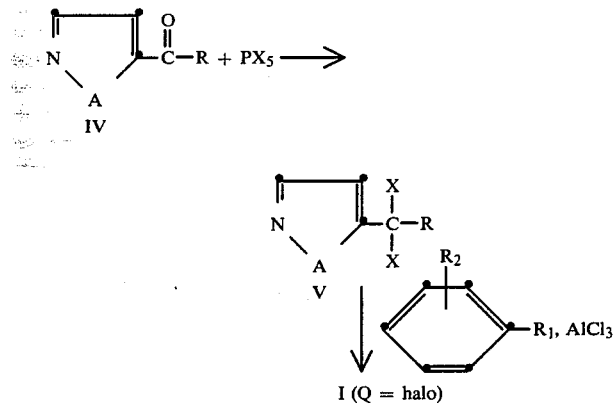

where X is chloro or bromo. According to this reaction, the ketone of formula IV is transformed into the dihalo derivative V upon treatment with a phosphorus pentahalide derivative by standard methods known in the art. Intermediate V is then reacted in the presence of at least one molar equivalent of aluminum chloride with the appropriately substituted benzene derivative to form the compound of formula I wherein Q is bromo or chloro. In this Friedel-Crafts reaction, either a non-reactive solvent may be employed, such as carbon disulfide, or an excess of the benzene reagent may be used as a solvent in addition to being the reactant.

Another method of preparing the carbinol derivative of Formula I is summarized by the following scheme:

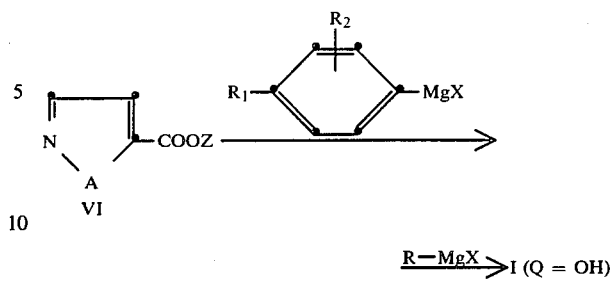

where Z is, for instance, $C_1$–$C_3$ alkyl. According to this scheme, an ester of a 5-azolecarboxylic acid (VI) is treated sequentially with the appropriate Grignard reagents following standard procedures to provide the desired carbinol derivative. The Grignard reagents may be added in either order and, if desired, the intermediate after the first reaction may be isolated before reacting it further. The reaction is generally carried out with the magnesium chloride or bromide derivatives in a non reactive solvent such as an ether. For obvious reasons, equimolar amounts of each reagent are employed.

Intermediate compounds II, III, IV, V, and VI as well as the other necessary reagents are either commercially available, are known in the literature, or can be prepared by methods known in the art.

In addition to the above reaction schemes, many of the compounds of Formula I can be transformed into other compounds of Formula I. For example, when Q is hydrogen, the compounds can be prepared according to the procedure of U.S. Pat. No. 2,727,895 whereby the corresponding carbinol (Q=hydroxy) is heated in a mixture of glacial acetic acid and aqueous hydriodic acid to reduce the hydroxyl group and yielded the corresponding methane derivative. Conversely, the methane derivative can be treated in basic solution with air or oxygen to prepare the corresponding carbinol derivative. The halo compounds can be prepared from the carbinol derivatives by treatment with a suitable halogenating reagent, such as a thionyl halide or an N-halosuccinimide. The compounds wherein Q is methyl can be prepared from the corresponding compounds wherein Q is hydrogen by alkylation with a methyl halide following the general liquid ammonia/alkali metal amide procedure as is described in U.S. Pat. No. 2,727,895.

In order to more fully illustrate the preparation of the compounds of this invention, the following examples are provided. The examples are illustrative only and are not intended to limit the scope of the invention in any way.

EXAMPLE 1

α,α-Bis(4-chlorophenyl)-5-isothiazolemethanol

To a solution of 1.0 g of isothiazole in 20 ml of tetrahydrofuran were added 8.1 ml of a 1.52M solution of n-butyllithium in hexane at −78° C. The mixture was allowed to stir for 15 minutes at which time 3.2 g of 4,4'-dichlorobenzophenone were added as a solution in 25 ml of tetrahydrofuran. The reaction was allowed to warm to room temperature and was stirred for 2 hours. Twenty-five milliliters of a saturated ammonium chloride solution were added and the tetrahydrofuran was removed by evaporation. The resulting mixture was extracted three times with ethyl acetate. The combined organic extracts were washed with a saturated ammonium chloride solution, water, and a saturated sodium chloride solution, dried over magnesium sulfate and evaporated. The resulting oil was chromatographed over silica gel. The appropriate fractions were combined and evaporated resulting in an oil. Cyclohexane was added and 1.21 g of the desired title product were recovered by filtration as white crystals, m.p. 118°–119.5° C.

Analysis for $C_{16}H_{11}Cl_2NOS$: Calc.: C, 57.15; H, 3.30; N, 4.17; Found: C, 57.17; H, 3.07; N, 4.17.

EXAMPLES 2–3

Following the procedure of Example 1, the following compounds were prepared from isothiazole and the appropriate benzophenone derivative.

2. α,α-Diphenyl-5-isothiazolemethanol, 55% yield, m.p. 127° C.

Analysis for $C_{16}H_{13}NOS$: Calc.: C, 71.87; H, 4.90; N, 5.24; Found: C, 71.62; H, 5.16; N, 4.95.

3. α-(2,4-Difluorophenyl)-α-phenyl-5-isothiazolemethanol, 33% yield as a glass.

Analysis for $C_{16}H_{11}F_2NOS$: Calc.: C, 63.36; H, 3.66; N, 4.62; Found: C, 63.48; H, 3.78; N, 4.86.

The compounds of this invention are useful in preventing or therapeutically treating estrogen-dependent diseases, including breast cancer, in mammals by virtue of their ability to inhibit the enzyme aromatase. Their ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of the above formula are summarized in Table 1.

TABLE 1

| Aromatase Inhibition in the Rat Ovarian Microsome Assay | |
|---|---|
| Compound of Example | EC$_{50}$* |
| 1 | <0.05 |
| 2 | 4.45 |

*Concentration of compound in μM required to achieve 50% inhibition of aromatase activity when substrate concentration is 0.1 μM.

By virtue of their ability to inhibit the enzyme aromatase, the compounds of this invention are able to inhibit the synthesis of estrogens in mammals, thereby making the compounds useful in the treatment of estrogen-dependent diseases, such as breast cancer. This activity was demonstrated in the following in vivo test system.

Estrogen Synthesis Inhibition in Rats

Immature female Wistar rats (44–55 grams) were divided into control and test groups of 5–8 animals each. Test compounds were administered for seven days as a component of the diet. Control animals received diet without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol.

After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls. Ovaries from rats treated with [$^3$H]-testosterone were excised, cleaned of extraneous tissue, and homogenized in 2.5 ml of a 1.0 mM potassium phosphate buffer containing 3.0 mM MgCl$_2$.6H$_2$O, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 (v/v) toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded and the pellet was dissolved in 0.3N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked and the plates were sprayed with primulin (0.001% in 4:1 v/v acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

TABLE 2

Effects of a Compound of Formula I on estrogen levels and uterine weight

| Test No. | Compound | Dose* | Animals | Mean Uterine Weight (mg) | Mean Steroid Concentration** | | |
|---|---|---|---|---|---|---|---|
| | | | | | estradiol | estrone | estriol |
| I | α,α-bis(4-chlorophenyl)-5-isothiazolemethanol | 200 | 5 | 110.8+ | 1.18 | 0.44 | 0.88+ |
| | Testosterone-treated control | — | 8 | 203.4 | 1.70 | 0.19 | 0.25 |
| | Corn oil control | — | 7 | 171.0 | — | — | — |

*ppm in feed. 200 ppm corresponds to approximately 20 mg/kg/day.
**femtomoles per milligram of protein.
+significantly different from testosterone-treated control, $p < 0.05$.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the above formula.

Such pharmaceutical compositions comprise as active ingredient from about 1 to about 95 percent by weight of a compound of the above formula associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 4

Hard gelatin capsules are prepared using the following ingredients:

| | per capsule |
|---|---|
| α,α-bis(4-fluorophenyl)-5-isothiazolemethanol | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 5

Capsules each containing 20 mg of medicament are made as follows:

|  | per capsule |
| --- | --- |
| 5-[(4-trifluoromethylphenyl)-(4-chlorophenyl)methyl]isoxazole | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 6

Capsules each containing 100 mg of active ingredient are made as follows:

|  | per capsule |
| --- | --- |
| α,α-bis(4-trifluoromethylphenyl)-5-isoxazolemethanol | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 7

Tablets each containing 10 mg of active ingredient are made up as follows:

|  | per tablet |
| --- | --- |
| 5-[1-(4-bromophenyl)-1-(3-methoxyphenyl)ethyl]isothiazole | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 8

A tablet formula is prepared using the ingredients below:

|  | per tablet |
| --- | --- |
| α-(3,4-dichlorophenyl)-α-(3-pyridyl)-5-isoxazolemethanol | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 9

Suppositories each containing 25 mg of active ingredient are made as follows:

|  | per suppository |
| --- | --- |
| 5-[(4-flurophenyl)(4-chlorophenyl)chloromethyl]isoxazole | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 10

Suspensions each containing 5 mg of medicament per 5 ml dose are made as follows:

|  | per 5 ml of suspension |
| --- | --- |
| 5-[(3-iodo-4-isopropylphenyl)-(2-ethoxy-4-nitrophenyl)methyl]isothiazole | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 11

An aerosol solution is prepared containing the following components:

|  | Weight % |
| --- | --- |
| α-(4-nitrophenyl)-α-(4-trifluoromethylphenyl)-5-isothiazolemethanol | 0.25 |
| Ethanol | 29.75 |
| Propellant 22 (Chlorodifluromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A compound of the formula

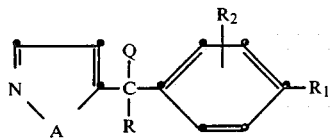

wherein:
A is S or O;
R is pyridyl or

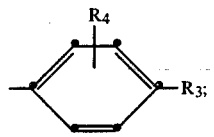

Q is hydrogen, hydroxy, halo, or methyl; and
$R_1$, $R_2$, $R_3$, and $R_4$ are independently hydrogen, halo, $C_1$–$C_3$ alkyl, $C_1$–$C_3$ alkoxy, nitro, or trifluoromethyl, and pharmaceutically acceptable salts thereof.

2. A compound of claim 1 wherein R is

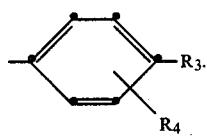

3. A compound of claim 2 wherein $R_1$ and $R_3$ are independently chloro, fluoro, or trifluoromethyl.

4. The compound of claim 3 which is α,α-bis(4-chlorophenyl)-5-isothiazolemethanol or a pharmaceutically acceptable salt thereof.

5. A method of inhibiting aromatase in a mammal which comprises administering to said mammal an aromatase inhibiting amount of a compound of claim 1.

6. The method according to claim 5 employing a compound wherein R is

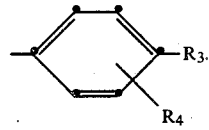

7. The method according to claim 6 employing a compound wherein $R_1$ and $R_3$ are independently chloro, fluoro, or trifluoromethyl.

8. The method according to claim 7 employing α,α-bis(4-chlorophenyl)-5-isothiazolemethanol or a pharmaceutically acceptable salt thereof.

9. A pharmaceutical formulation comprising a compound of claim 1 in association with a pharmaceutical carrier, diluent or excipient.

10. A formulation according to claim 9 employing a compound wherein R is

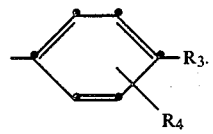

11. A formulation according to claim 10 employing a compound wherein $R_1$ and $R_3$ are independently chloro, fluoro, or trifluoromethyl.

12. A formulation according to claim 11 employing α,α-bis(4-chlorophenyl)-5-isothiazolemethanol or a pharmaceutically acceptable salt thereof.

* * * * *